United States Patent [19]

Barnett et al.

[11] Patent Number: 5,037,761
[45] Date of Patent: Aug. 6, 1991

[54] METHOD OF APPLYING AN AUTOMOTIVE TYPE OXYGEN SENSOR FOR USE IN AN INDUSTRIAL PROCESS ANALYZER

[75] Inventors: Daniel C. Barnett, Concord Township, Lake County; John J. Fry; George R. Hall, II, both of Wickliffe; David F. Ross, Euclid; Robert A. Smith, Mentor; Gordon D. Woolbert, North Canton, all of Ohio

[73] Assignee: Elsag International B.V., Amsterdam-Zuidoost, Netherlands

[21] Appl. No.: 335,605

[22] Filed: May 8, 1989

Related U.S. Application Data

[62] Division of Ser. No. 92,868, Sep. 3, 1987, abandoned.

[51] Int. Cl.$^5$ .............................................. G01N 25/00
[52] U.S. Cl. ................................... 436/137; 436/143; 436/149; 436/151; 436/155; 422/94; 422/95; 422/98; 204/408; 204/425; 204/153.18; 338/34
[58] Field of Search ............... 436/137, 143, 149, 151, 436/155; 422/94, 95, 98; 204/425, 408, 153.18; 73/23.32; 338/34

[56] References Cited

U.S. PATENT DOCUMENTS

| | | | |
|---|---|---|---|
| 3,558,280 | 1/1971 | Panson et al. | 436/151 |
| 3,720,594 | 3/1973 | Wilson | 204/195 S |
| 4,005,001 | 4/1977 | Pebler | 204/195 |
| 4,620,437 | 11/1986 | Takami et al. | 338/34 |
| 4,663,017 | 5/1987 | Ross | 204/409 |
| 4,703,646 | 11/1987 | Müller et al. | 338/34 |
| 4,713,696 | 12/1987 | Sunano et al. | 338/34 |
| 4,752,761 | 6/1988 | Dolan et al. | 338/34 |
| 4,829,810 | 5/1989 | Anderson et al. | 338/34 |
| 4,844,788 | 7/1989 | Takahashi et al. | 338/34 |

FOREIGN PATENT DOCUMENTS 0078942  3/1990  Japan .............................. 73/23.32

Primary Examiner—Robert J. Warden
Assistant Examiner—Laura E. Collins
Attorney, Agent, or Firm—Vytas R. Matas; Robert J. Edwards; Daniel S. Kalka

[57] ABSTRACT

An industrial process oxygen analyzer, and method of using same, incorporates an automotive oxygen sensor to minimize the criticalness of controlling heater temperature during operation. Higher sensor heater temperature, required to accommodate the automotive oxygen sensor, is achieved by application of higher supply voltage to the sensor heater. Current limiting of the heater supply circuit reduces stress on the sensor heater, even at the higher operating temperature.

7 Claims, 2 Drawing Sheets

METHOD OF APPLYING AN AUTOMOTIVE TYPE OXYGEN SENSOR FOR USE IN AN INDUSTRIAL PROCESS ANALYZER

This is a division of application Ser. No. 07/092,868 filed Sept. 3, 1987 now abandoned.

TECHNICAL FIELD

The present invention relates to the use of an oxygen sensor in industrial process control and more particularly to the use of an automotive type oxygen in an industrial process analyzer.

BACKGROUND ART

Oxygen analyzers are used extensively in industrial process control. When used in such control applications, these analyzers typically incorporate three major components—a zirconium dioxide sensor which produces a voltage output signal representative of oxygen concentration within the gas sample being analyzed, a heater to elevate the temperature of the sensor to a required operating temperature, and a heater control circuit to maintain the sensor temperature independent of environment. It has been found that the use of a typical zirconium oxide sensor for industrial process control has a number of inherent disadvantages. For example, typically the use of such a sensor requires the utilization of many associated parts, clamps, seals and fasteners making assembly and/or replacement a difficult task. In addition, it has been found that tight gas seals are difficult to maintain. Also, alignment of the components comprising the assembly is difficult to achieve and maintain. The zirconium dioxide sensor must be located in the gas stream and the heater and thermocouple must be aligned with the sensing tip. It has been further found that exposure of the heater element to the corrosive gas stream reduces heater life. And lastly, complex heater control circuitry is required because of the low mass of the heater. Temperature control is critical to prevent deviations of the sensor output.

Because of the foregoing, it has become desirable to develop a simplified system for analyzing the oxygen content of a gas utilized in an industrial process. Such a simplified system should minimize the criticalness of controlling heater temperature within the sensor.

SUMMARY OF THE INVENTION

The present invention solves the problems associated with the prior art and other problems by utilizing an autotive type oxygen sensor in place of the costly zirconium dioxide sensor typically used to determine the oxygen content of a gas, in an industrial process. The use of such an automotive type oxygen sensor requires a higher operating temperature than that normally required for a zirconium dioxide sensor, but sensor heater temperature is not nearly as critical. Such a higher operating temperature is achieved by applying a higher supply voltage to the sensor heater than typically used and by utilizing a current limiting circuit in conjunction with the higher supply voltage. The use of a higher supply voltage does not decrease heater life since current levels are actually less than that experienced with a lower supply voltage.

DESCRIPTION OF THE PREFERRED EMBODIMENT

Figure 1:
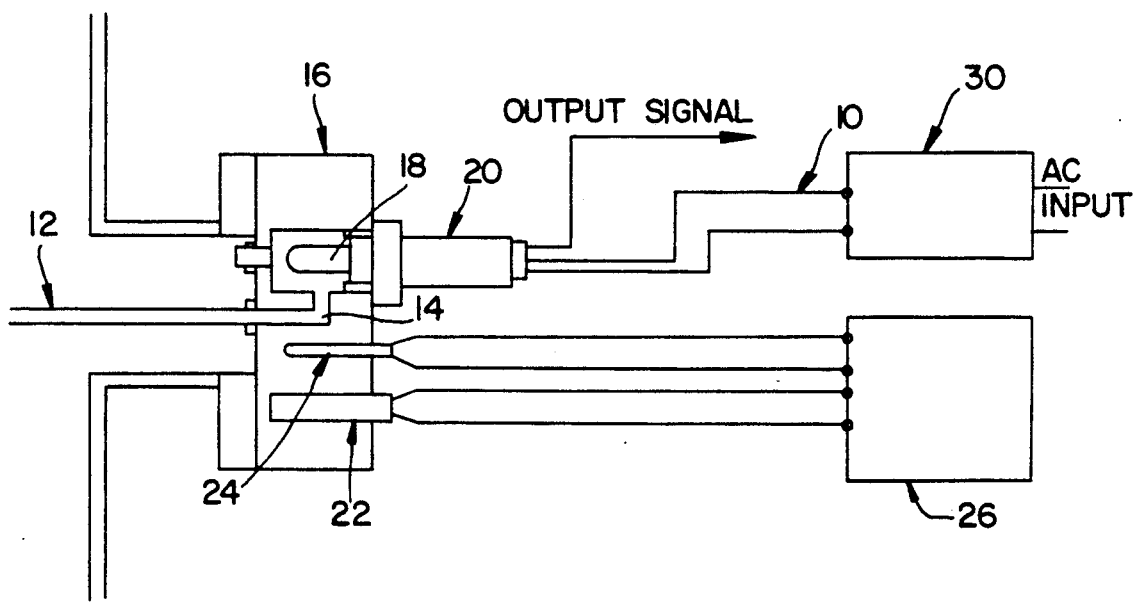
FIG. 1 is a schematic diagram showing the use of an automotive type oxygen sensor in conjunction with an associated power supply to analyze the oxygen content of a gas in an industrial process.

Referring now to the drawings where the illustrations are for the purpose of describing the preferred embodiment of the present invention and are not intended to limit the invention hereto, FIG. 1 is a schematic diagram of a system 10 for analyzing the oxygen content of an industrial process by using an automotive type oxygen sensor 20. In this system 10, a gas sample is drawn from the monitored industrial process through a sample probe, shown generally by the numeral 12. The drawing of this sample is typically accomplished through the use of an air powered aspirator (not shown) within the oxygen analyzer. The gas sample is directed through a passageway 14 in the analyzer manifold 16 across the sensor element 18 of the automotive type oxygen sensor 20 and is exhausted back into the gas flow within the industrial process. The analyzer manifold 16 is controlled at a substantially constant temperature above the gas stream dew point, typically 300 degrees to 600 degrees F. (149 degrees to 316 degrees C.). The controlled manifold temperature provides a substantially constant ambient temperature for the automotive type oxygen sensor 20. The analyzer manifold 16 is heated by heaters 22 and controlled by a temperature sensing element 24 which is connected to a temperature control circuit 26. An integral heater (not shown) within the automotive type oxygen sensor 20 is connected to a power supply 30 which is adjusted to provide the desired operating temperature at the sensor element 18 of automotive type oxygen sensor 20. The operating temperature of the sensor element 18 is dependent upon the process being monitored but is typically between 1300 degrees to 1500 degrees F. (704 degrees to 816 C.).

When an automotive type oxygen sensor 20 is used, the temperature of the sensor element 18 is not critical since sensor is used only as a switch at or near stoichiometric conditions (excess air factor $\lambda = 1$). The switch occurs in the range of 200 to 500 mv output and can operate reliably anywhere above 350 degrees C. Analyzing industrial processes for percent oxygen content requires accurate measurements above the $\lambda = 1$ control range to 100% excess air. Higher operating temperature is required to raise the mvdc output level to a usable span over this range and also to minimize the effect of interfering gases such as sulfur dioxide. This higher operating temperature is achieved by applying a higher supply voltage to the heater within the automotive type oxygen sensor 20 while limiting the current thereto. Such a higher supply voltage is provided by the power supply 30 as hereinafter described.

Figure 2:
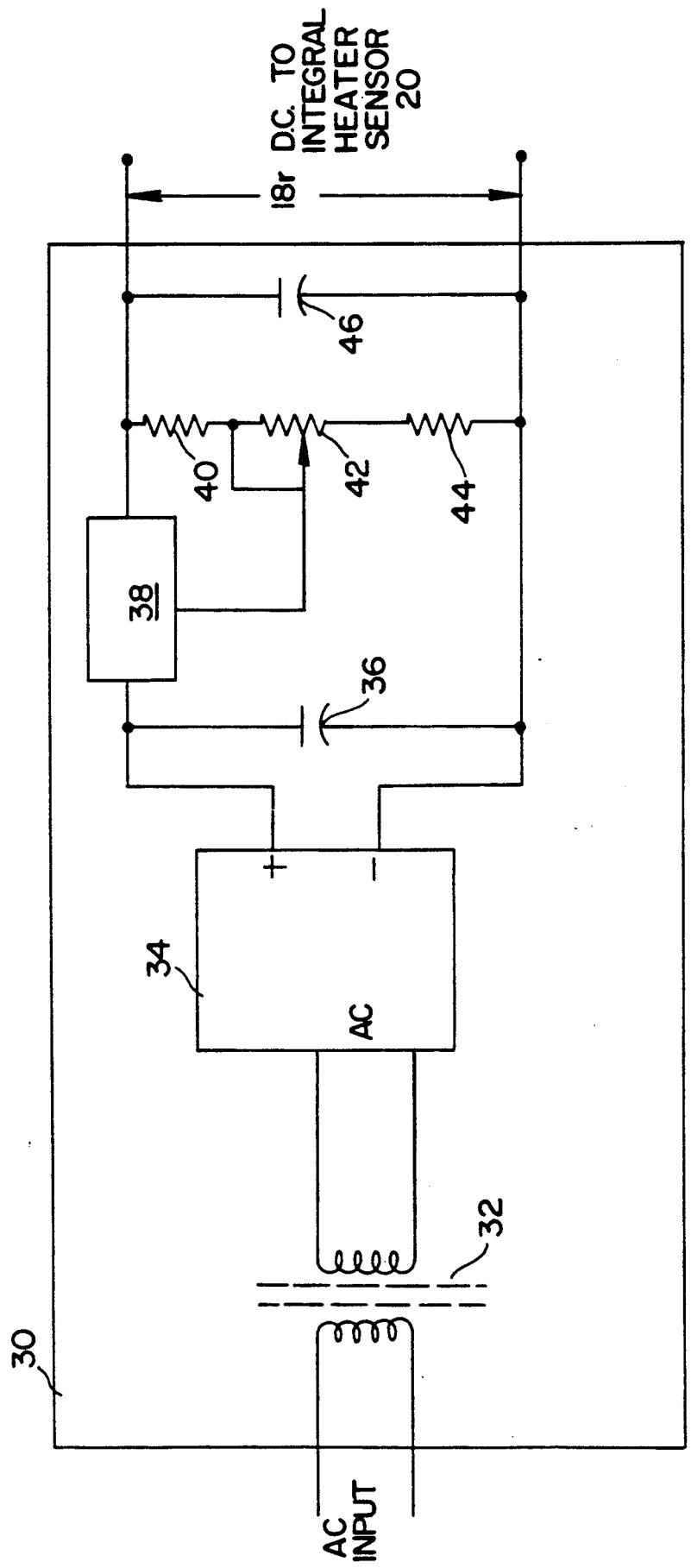
FIG. 2 is an electrical schematic drawing of the power supply for the automotive type oxygen sensor utilized to analyze the oxygen content of a gas in an industrial process.

Referring now to FIG. 2 which is an electrical schematic of power supply 30, this power supply converts 120 volts AC 50/60 Hz AC line power to the 18 VDC, 1 amp level required by the heater within the automotive type oxygen sensor 20. This power supply also limits the current supplied to the heater under cold start-up conditions. This power supply 30 includes a transformer 32 which converts the 120 volts AC line input to a voltage which is somewhat greater than the voltage typically utilized by the sensor heater. A bridge rectifier 34 and capacitor 36 convert the AC input to the transformer 32 to a DC voltage which is applied to a voltage regulator 38 which, in turn, regulates the DC voltage to a level determined by a series of resistors 40, 42 and 44. Capacitor 46 is connected across the combination of resistors 40, 42 and 44 to provide additional filtering and stability to the circuit. The combination of resistors 40, 42 and 44 allows the output voltage of the circuit to be varied according to installation requirements.

During normal operation, the power supply 30 supplies the nominal 18 volts DC and 1 ampere power required by the sensor heater. During cold start-up conditions, a current limiting mechanism, which is an integral part of voltage regulator 38, varies the output voltage of the power supply 30 so that the maximum current through the sensor heater does not exceed approximately 2.2 amps.

Controlling sensor heater voltage through the output voltage of the power supply 30 provides several distinct advantages. First, the heater voltage is controlled much more closely than in typical automotive applications thus making the oxygen concentration measurement considerably more accurate. In addition, the voltage which is applied to the heater is somewhat higher than the nominal 12 to 14 volts typically used in an automotive application allowing the heater to reach a higher operating temperature permitting the automotive type oxygen sensor to be used in an industrial process control application. And lastly, the current limiting ability of the power supply reduces the stress on the heater during cold start-up conditions.

The possibility of using an automobile type oxygen sensor in an industrial process control application provides several inherent advantages. For example, the oxygen sensor 20 threads directly into the analyzer manifold 16 and seals with only one captive spark plug type seal. No alignment is required with respect to a separate heater, thermocouple or gas stream as is typically required with present industrial oxygen analyzers. By using an automotive type oxygen sensor, the integral internal heating element is not exposed to corrosive process gases, thus extending heater life. The positive temperature coefficient of the heater element used in an automotive type oxygen sensor aids is current limiting of the heater as the operating temperature is approached. Current limiting of the heater supply circuit provides cold start-up current protection thus allowing for higher voltage operation (18 volts DC typical) than in automotive applications (13.5 volts DC typical). This, in turn, requires less ambient temperature control (300 degrees F. typical) for the analyzer manifold to obtain the required operating temperature (1300 degrees F. typical) for the heater. Temperature control of the higher mass, lower temperature analyzer manifold, instead of the smaller sensor heater, simplifies the heater control circuitry. And lastly, the more rugged design of the automotive type oxygen sensor greatly reduces the possibility of breakage of time.

Certain modifications and improvements will occur to those skilled in the art upon reading the foregoing. It should be understood that all such modifications and improvements have been deleted herein for the sake of conciseness and readability, but are properly within the scope of the following claims.

I claim:

1. A method of analyzing the oxygen content of a gas, comprising the steps of:

situating an automotive type oxygen sensor in an analyzer manifold, the automotive type oxygen sensor having a sensor element and integral electric heating means;

maintaining the sensor element within a predetermined operating temperature range by applying a voltage to the integral electric heating element of the automotive type oxygen sensor, said voltage being greater than about 12 volts;

directing a gas sample through the analyzer manifold to the sensor element of the automotive type oxygen sensor to obtain an output millivolt D.C signal therefrom indicative of the oxygen content of the gas sample; and limiting the current applied to the automotive type oxygen sensor during start-up to extend the life of the sensor.

2. The method according to claim 1, wherein the predetermined operating temperature range of the sensor element is between 1300 degrees F. and 1500 degrees F.

3. The method according to claim 1, further including the step of maintaining the temperature of the analyzer manifold at a substantially constant temperature above the dew point temperature of the gas sample.

4. The method according to claim 1, wherein the voltage applied to the integral heating element of the automotive type oxygen sensor is about 18 volts D.C. and the current level is about 1 ampere during normal operation.

5. The method according to claim 1, wherein the maximum current through the integral heating element is initially limited to not exceed approximately 2.2 amperes during start-up conditions.

6. A method of analyzing the oxygen content of a gas, comprising the steps of:

situating an automotive type oxygen sensor in an analyzer manifold, the automotive type oxygen sensor having a sensor element and integral electric heating means;

maintaining the sensor element within a predetermined operating temperature range by applying a voltage to the integral electric heating element of the automotive type oxygen sensor, said voltage being greater than about 12 to 14 volts;

directing a gas sample through the analyzer manifold to the sensor element of the automotive type oxygen sensor to obtain an output millivolt D.C. signal therefrom indicative of the oxygen content of the gas sample; and limiting the current initially applied to the automotive type oxygen sensor for extending the life of the sensor.

7. A method of analyzing the oxygen content of a gas, comprising the steps of:

situating an automotive type oxygen sensor in an analyzer manifold maintained at a constant temperature of about 1300° F. to about 1500° F., the automotive type oxygen sensor having a sensor element and integral electric heating means;

maintaining the sensor element within a predetermined operating temperature range by applying approximately 18 volts D.C. to the integral electric heating element of the automotive type oxygen sensor;

directing a gas sample through the analyzer manifold to the sensor element of the automotive type oxygen sensor to obtain an output millivolt D.C. signal therefrom indicative of the oxygen content of the gas sample; and limiting the current applied to the automotive type oxygen sensor during start-up for extending the life of the sensor.

* * * * *